US009714923B2

(12) United States Patent
Behmlander et al.

(10) Patent No.: US 9,714,923 B2
(45) Date of Patent: Jul. 25, 2017

(54) TOPOGRAPHIC WEAR MONITORING SYSTEM FOR GROUND ENGAGING TOOL

(71) Applicant: Caterpillar Inc., Peoria, IL (US)

(72) Inventors: Matthew Jacob Behmlander, Metamora, IL (US); Terri Lynn Atkinson, Farmington, IL (US); Jeremy Roe Hammar, Metamora, IL (US)

(73) Assignee: Caterpillar Inc., Peoria, IL (US)

( * ) Notice: Subject to any disclaimer, the term of this patent is extended or adjusted under 35 U.S.C. 154(b) by 6 days.

(21) Appl. No.: 14/707,173

(22) Filed: May 8, 2015

(65) Prior Publication Data

US 2016/0326723 A1 Nov. 10, 2016

(51) Int. Cl.
| E02F 9/26 | (2006.01) |
| E02F 9/28 | (2006.01) |
| G01N 29/04 | (2006.01) |
| G01N 29/26 | (2006.01) |
| G01N 29/34 | (2006.01) |

(52) U.S. Cl.
CPC ........... *G01N 29/043* (2013.01); *E02F 9/268* (2013.01); *E02F 9/2825* (2013.01); *E02F 9/2833* (2013.01); *G01N 29/262* (2013.01); *G01N 29/343* (2013.01); *G01N 2291/0258* (2013.01); *G01N 2291/044* (2013.01); *G01N 2291/106* (2013.01)

(58) Field of Classification Search
CPC ........ E02F 9/26; E02F 9/2808; G01N 29/043; G01N 2291/044; G01N 2291/106
USPC .......................................................... 701/50
See application file for complete search history.

(56) References Cited

U.S. PATENT DOCUMENTS

| 3,817,647 A | 6/1974 | Lemelson |
| 3,963,364 A | 6/1976 | Lemelson |
| 4,711,120 A | 12/1987 | Kwun et al. |
| 4,738,139 A | 4/1988 | Blessing et al. |
| 6,990,390 B2 | 1/2006 | Groth et al. |
| 7,805,997 B2 | 10/2010 | Yu et al. |
| 8,688,331 B2 * | 4/2014 | Peterson ............. A01B 79/005 172/278 |
| 9,134,280 B2 * | 9/2015 | Cataldo ............... G01N 29/043 |
| 2004/0148057 A1 * | 7/2004 | Breed ................... B60Q 9/008 700/242 |
| 2004/0190374 A1 * | 9/2004 | Alft ....................... E21B 7/046 367/14 |
| 2006/0142936 A1 * | 6/2006 | Dix ..................... A01B 79/005 701/50 |

(Continued)

FOREIGN PATENT DOCUMENTS

DE 102012111722 A1 6/2014

*Primary Examiner* — Atul Trivedi
(74) *Attorney, Agent, or Firm* — Miller, Matthias & Hull

(57) ABSTRACT

A system for measuring topography of the surface of a ground engaging tool is disclosed. The system may include a machine and the ground engaging tool. A phased array ultrasonic sensor may be associated with the ground engaging tool and configured to create ultrasonic pulses within the ground engaging tool. A communication device may be associated with the phased array ultrasonic sensor. A monitoring component may communicate with the phased array ultrasonic sensor via the communication device, and may be configured to receive signals from the phased array ultrasonic sensor and monitor the topography of the ground engaging tool.

20 Claims, 4 Drawing Sheets

(56) References Cited

U.S. PATENT DOCUMENTS

| | | | |
|---|---|---|---|
| 2008/0121040 A1* | 5/2008 | MacLauchlan | G01N 29/265 73/618 |
| 2008/0141778 A1* | 6/2008 | Bosselmann | G01B 15/00 73/633 |
| 2008/0153402 A1* | 6/2008 | Arcona | B24B 7/188 451/352 |
| 2008/0177449 A1* | 7/2008 | Pickett | A01D 41/141 701/50 |
| 2009/0268553 A1* | 10/2009 | Ecker | G01S 7/003 367/119 |
| 2010/0300059 A1* | 12/2010 | Haws | A01D 45/007 56/327.2 |
| 2012/0227992 A1* | 9/2012 | Henry | A01B 63/114 172/4 |
| 2013/0197743 A1* | 8/2013 | Lindskov | E02F 9/2025 701/34.4 |
| 2013/0341056 A1* | 12/2013 | Casper | A01B 63/111 172/4 |
| 2013/0345937 A1* | 12/2013 | Strelioff | A01M 7/0057 701/50 |
| 2014/0190046 A1* | 7/2014 | Shibata | E02F 3/964 37/403 |
| 2014/0311762 A1 | 10/2014 | Behmlander et al. | |
| 2015/0033595 A1* | 2/2015 | Chenoweth | E02F 9/2841 37/455 |
| 2015/0066291 A1* | 3/2015 | Johannsen | B62D 55/32 701/34.4 |
| 2015/0081166 A1* | 3/2015 | Diekevers | B62D 55/14 701/34.4 |
| 2015/0292179 A1* | 10/2015 | Joergensen | G01C 15/004 701/50 |
| 2015/0343644 A1* | 12/2015 | Slawinski | B25J 11/008 701/2 |

* cited by examiner

TOPOGRAPHIC WEAR MONITORING SYSTEM FOR GROUND ENGAGING TOOL

TECHNICAL FIELD

The present disclosure relates generally to a wear monitoring system and, more particularly, to a topographic wear monitoring system for a ground engaging tool.

BACKGROUND

Machines, for example wheel loaders, track loaders, backhoes, and hydraulic excavators, mining shovels, electric rope shovels, draglines, and continuous miners are commonly used for excavating, mining, and material moving applications. Such machines generally include a ground engaging tool having a ground engaging surface that is configured to contact the material. During use of the ground engaging tool, the contacted material abrades the ground engaging surface of the tool. The abrasion results in wearing of the ground engaging surface. As a result, the ground engaging tool and/or a wear member that is part of the ground engaging tool often will be formed so as to be removable from the machine. Either the entire ground engaging tool or the wear member may be replaced on a periodic basis.

The ground engaging tool or its wear member may be replaced when it is determined that wear has occurred beyond an acceptable limit. The determination of when sufficient wear has occurred to indicate the need for replacement typically may be made by service personnel called out to inspect the machine. The determination may be made by visual inspection and measuring the dimensions of the ground engaging tool manually. The measured dimensions then may be compared to the acceptable limit, and selectively replaced based on the comparison. This process of determining when to replace the tool or wear member can be time consuming, labor intensive, and inaccurate.

Tool wear may have multiple consequences. For example, significant wear of one or more ground engaging tools may decrease the efficiency of a machine. Large machines may have large ground engaging tools of substantial weight, for example weights in hundreds of pounds or kilograms. Such large ground engaging tools add substantial cost to maintaining a machine at a large excavating or material moving site such as a quarry, since heavy use in highly abrasive materials may cause significant wear in a short period of time, for example a matter of days or even hours. In addition, heavy wear may cause tool failure, and where the machine is operating in conjunction with a crusher, a failed tooth may accidently be dumped into the crusher and cause serious damage. This may in turn cause significant down time and expense to the entire operation.

One way to measure tool wear is described in U.S. Patent Application Publication 2014/0311762 of Behmlander et al. that was published on Oct. 23, 2014 ("the '762 publication"). Specifically, the '762 publication discloses a sensor imbedded within a cutting edge of a ground engaging tool to measure the length of the tool. The sensor disclosed in the '762 publication is ultrasonic, and generates high frequency sound waves within the cutting edge and evaluates a resulting echo received back by the sensor. A calculation of the time interval between generating a sound wave and receiving an echo gives an indication of the length of the cutting edge. Comparison with a threshold length, in turn, gives an indication of the reduction in length and thus the amount of erosion that has occurred.

Although the wear sensor of the '762 publication may offer a way to monitor decrease in tool length, it's indication of wear may be improved upon. In particular, while the sensor of the '762 publication may provide a significant indication of wear by measuring a decrease in tool length, wear may occur in ways other than a decrease in length of a tool. For large ground engaging tools in heavy use with highly abrasive materials, wear may include alteration of the surface of the ground engaging tools in other ways. A measure of tool length may not necessarily give an indication of breakage of portions of the tool, a decrease in width or thickness of the tool, or other significant alterations of the working surface of the tool. Furthermore, while data on decrease in tool length may give excellent information relevant to strategic development of some tools, it may be beneficial to have data for other wear patterns in order to give additional indications of where the application of tougher alloys and/or hard facing materials may extend tool life.

The topographic wear monitoring system of the present disclosure addresses one or more of the needs set forth above and/or other problems of the prior art.

SUMMARY

In one aspect, the present disclosure is directed to a system for measuring topography of the surface of a ground engaging tool. The system may include a machine with an on-board station and the ground engaging tool. The system also may include a phased array ultrasonic sensor associated with the ground engaging tool of the machine and configured to direct ultrasonic pulses within the ground engaging tool. The system also may include a communication device associated with the phased array ultrasonic sensor, and a monitoring component associated with the on-board station and communicating with the phased array ultrasonic sensor via the communication device. The monitoring component may be configured to receive signals from the phased array ultrasonic sensor and monitor the topography of the surface of the ground engaging tool.

In another aspect, the present disclosure is directed to a ground engaging tool for a machine comprising a ground contacting surface surrounding a volume. A cavity may be within the ground engaging tool, and at least one phased array ultrasonic sensor may be located within the cavity and configured to sweep a beam of ultrasonic pulses through at least a portion of the volume of the ground engaging tool in at least one general direction to at least a portion of the ground contacting surface. The sensor may be configured to receive echoes from the surface portion indicative of the topography of the surface portion.

In another aspect, the present disclosure is directed to a machine, comprising an implement operatively associated with the machine, and with a ground engaging tool on the implement and including a ground engaging surface. A cavity may be located within the ground engaging tool, and at least three phased array ultrasonic sensors may be located within the cavity and configured to sweep beams of ultrasonic pulses through the ground engaging tool, with each of the three phased array ultrasonic sensors located and arranged to sweep beams in three generally, mutually perpendicular directions toward surface portions of the ground engaging tool located in the three directions. The sensors may be configured to receive echoes from the surface portions giving an indication of the topography of the ground engaging surface. A wireless communication device may be located in the cavity, and there may be at least one battery configured to power the wireless communication device and the three phased array ultrasonic sensors. A monitoring system may be configured to determine the topography of the surface of the ground engaging tool, make a comparison of the determined topography with a threshold topography, and generate a signal based on the result of the comparison.

DETAILED DESCRIPTION

Figure 1:
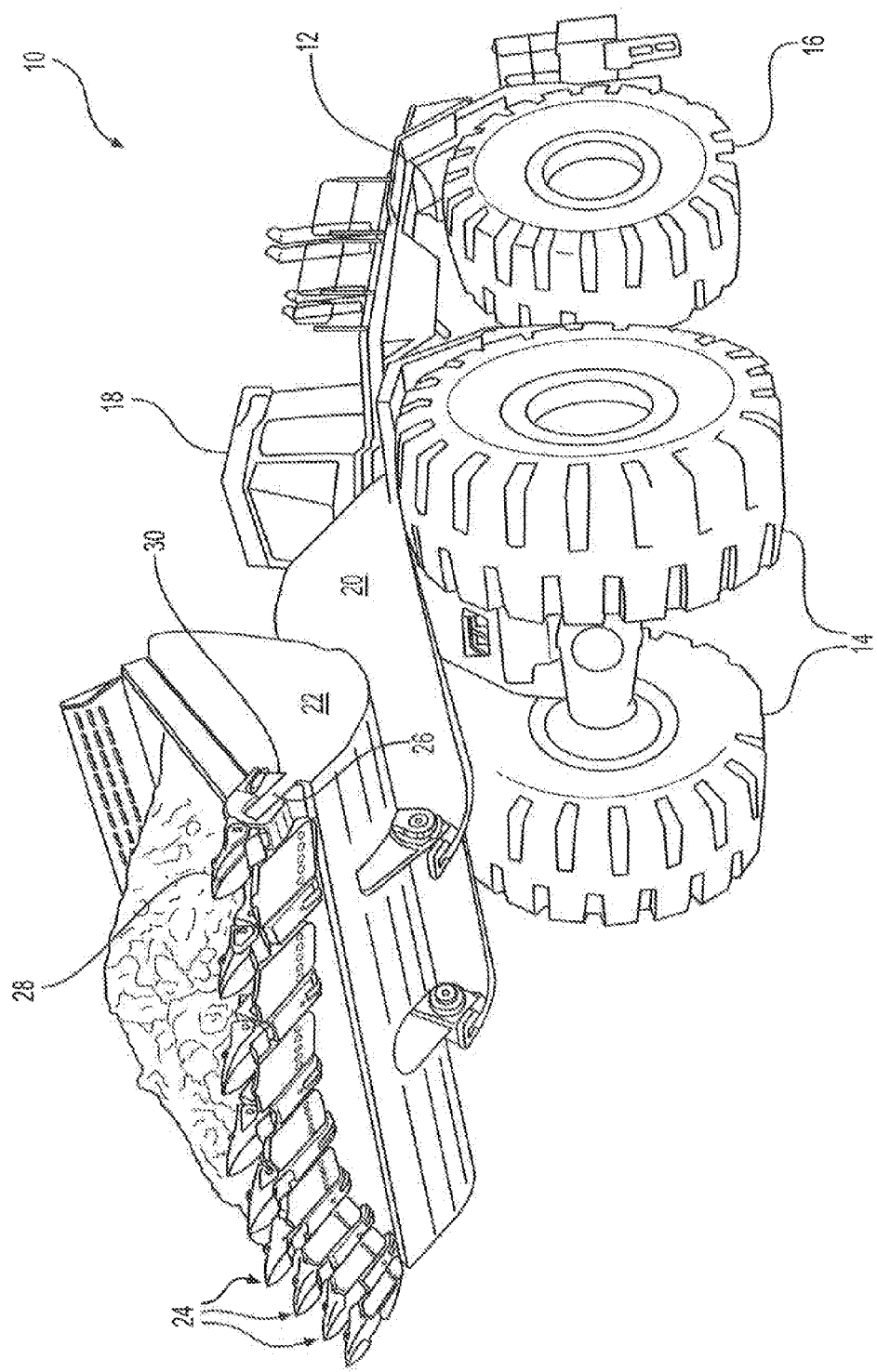
FIG. 1 is an isometric illustration of an exemplary disclosed machine.

An exemplary embodiment of a machine 10 is illustrated in FIG. 1. Machine 10 may be, for example, a wheel loader, a track loader, a backhoe, a hydraulic excavator, or any other type of machine known in the art. As a wheel loader, machine 10 may include a chassis 12 supported by a pair of front wheels 14 and a pair of rear wheels 16 (only one of which is shown). At least the front wheels 14 may be steerable, and chassis 12 may include front and rear frame portions that may be capable of relative articulation. Machine 10 may include an on-board operator station 18 which may provide accommodations for an operator and also may house control equipment that enables machine 10 to be operated remotely.

A lift linkage mechanism 20 may extend from the chassis 12, and may be capable of pivotal movement vertically adjacent its proximal end relative to chassis 12. A work implement 22, such as a scoop or bucket, may be attached adjacent the distal end of lift linkage mechanism 20, and may be capable of pivotal movement relative to lift linkage mechanism 20. Other types of lift linkage mechanisms and work implements capable of various movements are contemplated, depending on the type of machine and the type of work to be performed.

Figure 2:
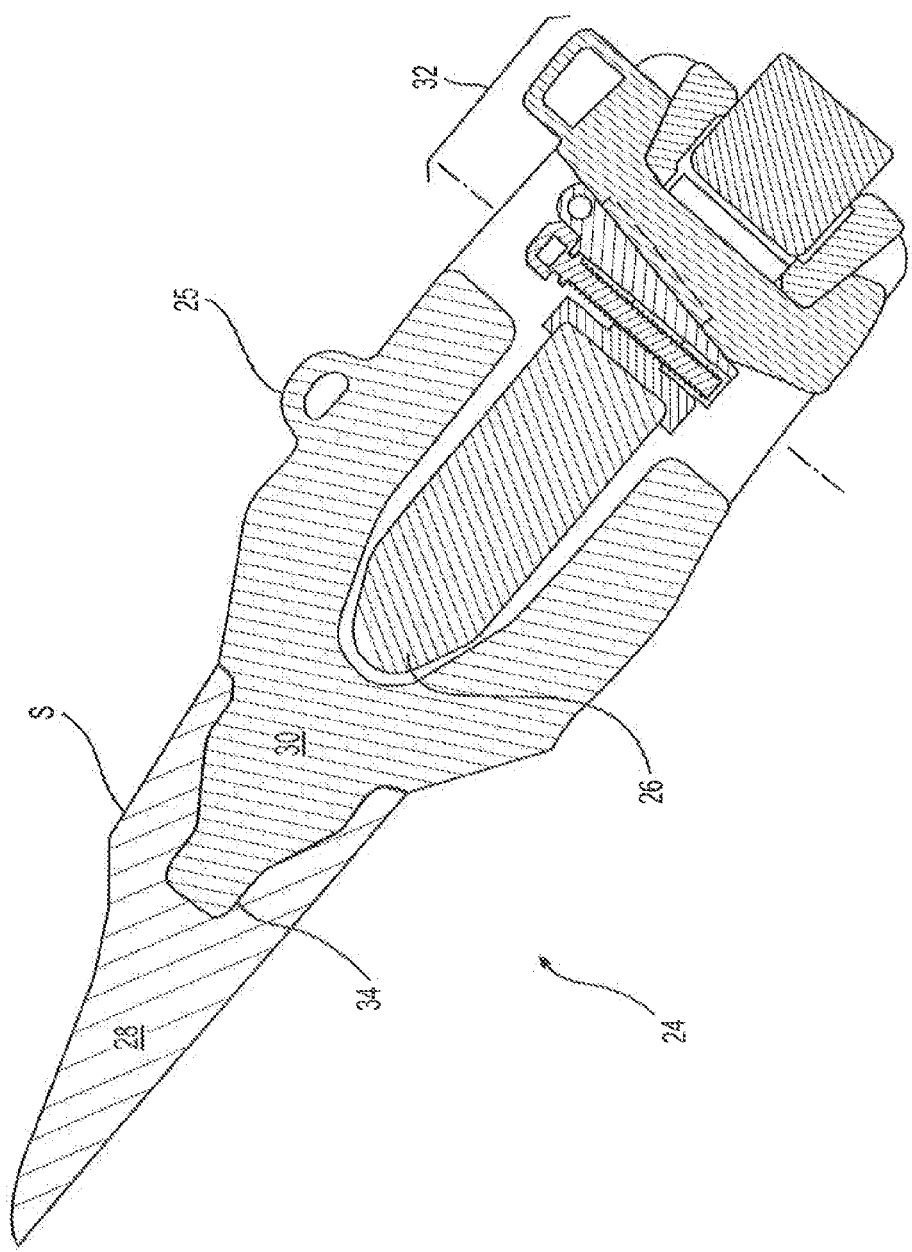
FIG. 2 is a cross-section of an exemplary disclosed work tool.

Work implement 22 may be equipped with one or more ground engaging tools (GET) 24 located at or adjacent to a cutting edge 26. For example, the disclosed bucket is illustrated as being provided with a plurality of similar tooth assemblies that are spaced apart along the length of cutting edge 26. GET 24 may be a single-piece component or a multi-piece component, e.g., a multi-piece tooth assembly, that may be removably connected to work implement 22. In the embodiment shown in FIG. 2, GET 24 is illustrated as a two-piece component having a wear tip 28 and an adapter 30 that are connected to cutting edge 26 of work implement 22 via a retention system 32 which may allow GET 24 to be removably connected to work implement 22. Details of the retention system 32 are not described inasmuch as numerous retention systems are known and any number of known retention systems could be employed. Wear tip 28 may be joined to a nose end 34 of adapter 30 in any manner known in the art, for example via welding, threaded fastening, or by a releasable retention system (analogous to retention system 32, for example) allowing for removal of wear tip 28 from adapter 30 and replacement with a new wear tip when necessary or desirable.

GET 24 may engage a material to be removed or excavated, and such engagement may cause GET 24 to wear away during use of machine 10. After surface S of GET 24 has worn by a predetermined threshold amount, GET 24 should be replaced to help ensure productivity and/or efficiency of machine 10. As noted above and as shown in FIG. 2, GET 24 may be removably connected to cutting edge 26 of the work implement 22 by way of retention system 32. GET 24 may be of a size and weight consistent with the size of machine 10 on which it may be mounted. For example, exemplary GET 24 illustrated in FIG. 2 includes a lifting eye 25 indicating a GET 24 that is large enough and heavy enough to require heavy equipment to manipulate it during mounting on and removal from work implement 22. Such massive GET components mounted on large machine in highly abrasive environments experience rapid topographic wear.

Figure 3:
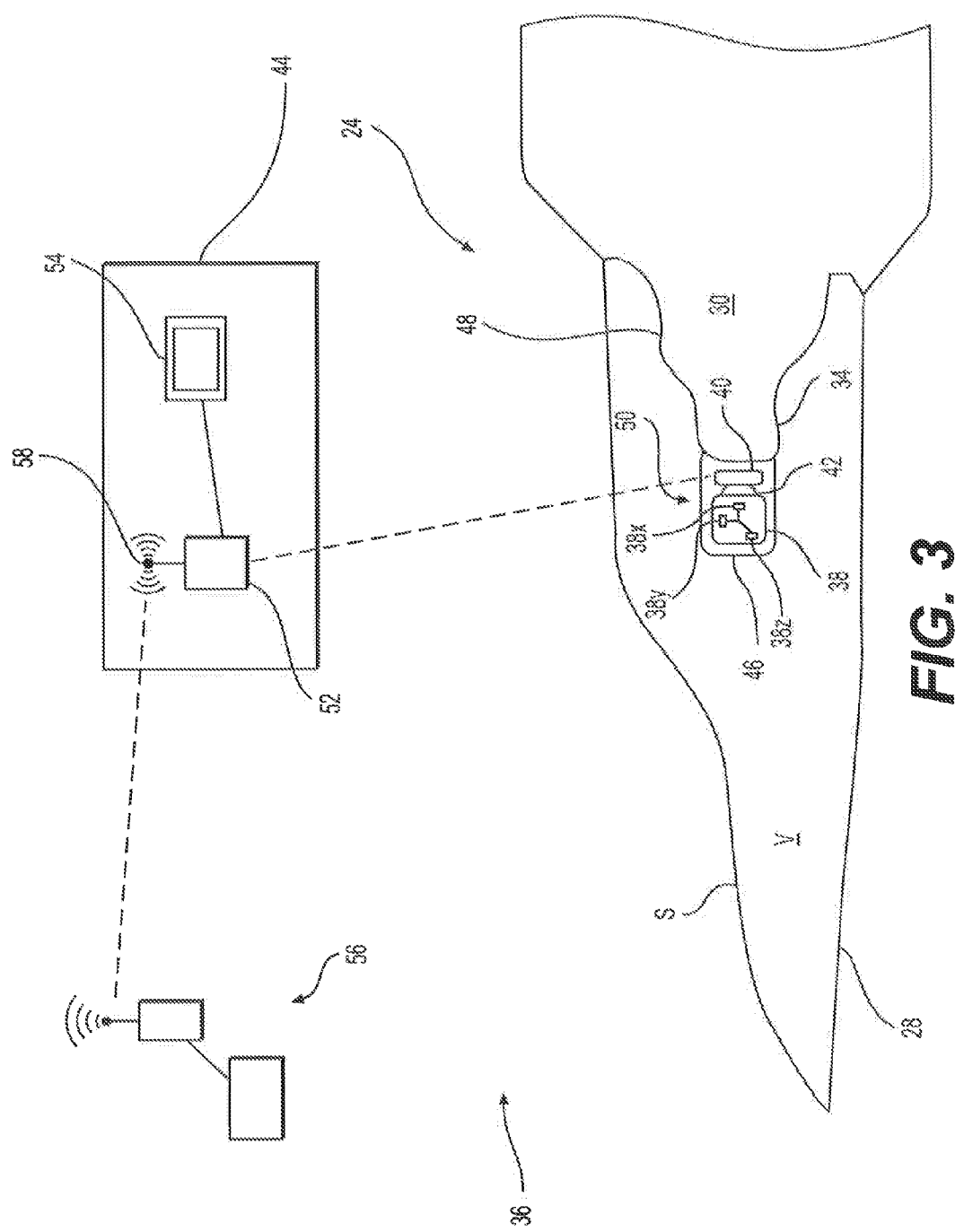
FIG. 3 is a diagrammatic illustration of an exemplary disclosed topographic wear monitoring system that may be used in conjunction with the machine of FIG. 1 and the work tool of FIG. 2.

FIG. 3 illustrates a topographic wear monitoring system 36 for measuring topography of the surface of a ground engaging tool, associated with machine 10. Topographic wear monitoring system 36 is configured to determine the topography of the surface of GET 24, make a comparison of the determined topography with a threshold topography, and generate a signal based on the result of the comparison. Topographic wear monitoring system 36 may have various components that cooperate to measure the topography of GET 24 and monitor topographic wear of GET 24. Topographic wear monitoring system 36 also may determine when to signal a warning that tool topography has changed significantly, may map the pattern of topographic wear over time, may shut down equipment upon significant change in tool topography or substantial failure of the tool, and may signal when tool maintenance or replacement may be due. While FIG. 3 illustrates topographic wear monitoring system 36 in connection with one GET 24 of an implement 22, it is contemplated that for some machines each GET 24 on implement 22 may include a similar topographic wear monitoring system 36.

Components of topographic wear monitoring system 36 may include, among other things, a phased array ultrasonic sensor associated with the ground engaging tool 24 of the machine 10 and configured to create ultrasonic pulses within the ground engaging tool. At least one phased array ultrasonic sensor 38 may be mounted within a cavity in GET 24. A communication device 40 may be associated with the phased array ultrasonic sensor 38. A battery 42 may be associated with and configured to deliver power to sensor 38 and communication device 40, and a monitoring component 44 may be associated with the on-board operator station 18 of machine 10 and communicating with phased array ultrasonic sensor 38 via communication device 40. Battery 42 may take any form known in the art, and may include multiple batteries. Communication device 40 may be any type of communication expedient known in the art capable of directing signals from sensor 38 to monitoring component 44 wirelessly, for example by standard 2.4 gigahertz wireless. The wireless communications may include satellite, cellular, infrared, and any other type of wireless communication.

Phased array ultrasonic sensor 38 may be located and attached within a cavity 46 formed in GET 24. Sensor 38 may be oriented so as to create pulses and sweep a beam in a direction generally toward the GET 24 surface portion whose topography is to be sensed. In one embodiment, the use of one phased array ultrasonic sensor 38, e.g. configured to direct ultrasonic pulses in at least one general direction within the ground engaging tool, may yield enough topographic data to sufficiently monitor wear of GET 24. In other embodiments, two, three, or more phased array ultrasonic sensors may be employed to ensure a total topographic measure of the surface of GET 24. For large machines where GET 24 may experience rapid topographic wear, it is contemplated that each GET 24 of implement 22 may be provided with one or more phased array ultrasonic sensors. Where more than one GET 24 of an implement 22 includes one or more phased array ultrasonic sensors, the sensor or sensors of each tooth may operate on different frequencies in order to reduce the chance of interference and error readings.

Phased array ultrasonic sensor 38 may be made up of an array of small elements generating high-frequency sound waves within GET 24. The small elements, or transducers, may be pulsed individually at a calculated timing. Sensor 38 may electronically control the sweep of a beam through a volume V of material of GET 24 at high speed. Sensor 38 may then evaluate resulting echoes received back from the surface S of GET 24, or a targeted surface portion thereof. Calculation of time intervals between pulses from sensor 38 and reception of echoes from the targeted surface portion, either by sensor 38 and/or by monitoring component 44, may enable determination of distances from sensor 38 to increments of the targeted surface portion and yield data giving an indication of surface topography. As the targeted surface portion of GET 24 wears, the time intervals may change, and sensor 38 may generate signals indicative of current topography and, over time, the change in topography of the targeted surface portion. These signals may be directed to monitoring component 44 for processing.

Referring to FIG. 3, illustrating a GET 24 that is a multi-piece component, cavity 46 is illustrated as an extended portion of the recess 48 within wear tip 28 that receives nose end 34 of adapter 30. In this embodiment, phased array ultrasonic sensor 38 (or plural such sensors where plural sensors are employed), battery 42, and wireless communication device 40 may be arranged in a package 50 and attached or mounted together within cavity 46 formed interiorly of GET 24 in wear tip 28 before assembly of wear tip 28 and adapter 30. Package 50 may be assembled and stocked, prior to installation within cavity 46 of GET 24, with a non-conductive tape or tab (similar to those employed in various toys with pre-installed batteries, for example) preventing battery contact with sensor 38 or communication device 40, and the tape or tab may be removed when package 50 is installed during manufacture of GET 24 in order to allow the battery to power sensor 38 and wireless communication device 40. Package 50 may take various shapes, such as generally cylindrical, generally rectangular, ovoid, etc.

In embodiments where joining of wear tip 28 and adapter 30 is substantially permanent (e.g., welding), the useful life of sensor 38, battery 42, and communication device 40 effectively may be equivalent to the useful life of GET 24. In other words, when GET 24 reaches the end of its useful life, package 50 may be scrapped along with the spent GET. In other embodiments where wear tip 28 is joined to adapter 30 by a releasable retention system, package 50 may be removed and replaced with a different package including a new sensor, battery, and communication device, or in the case of battery failure, a new battery may be installed.

While cavity 46 is illustrated as an extended portion of recess 48, it is contemplated that cavity 46 could take other forms. For example, it is contemplated that cavity 46 could be formed as a cavity separated from recess 48 and accessed via a separate opening at a location on the surface of wear tip 28. Such as opening may be permanently sealed or provided with a removable closure, for example a threaded cap. Additionally, it is contemplated that cavity 46 could be formed within adapter 30 so that package 50 would be in the adapter instead of wear tip 28. Furthermore, where GET 24 is a single-piece component rather than a multi-piece component, cavity 46 and package 50 may be situated in a cavity within that single-piece component.

The assessment of topographic wear of surface S of GET 24 may be enhanced by use of multiple phased array ultrasonic sensors. In other words, multiple phased array ultrasonic sensors may be mounted interiorly of the ground engaging tool with each of the multiple phased array ultrasonic sensors being configured to direct ultrasonic pulses in different general directions within the ground engaging tool. While a single sensor targeting one general surface portion of surface S may yield sufficient data in some cases, it may be more effective to include one or more additional phased array ultrasonic sensors in other cases. FIG. 3 diagrammatically illustrates an embodiment wherein three phased array ultrasonic sensors may be employed. In this embodiment, one phased array ultrasonic sensor is designated 38$x$, a second phased array ultrasonic sensor is designated 38$y$, and a third phased array ultrasonic sensor is designated 38$z$. This indicates that each respective sensor may be configured to sweep a beam of ultrasonic pulses through at least a portion of the volume V of the ground engaging tool 24 in at least one general direction to at least a portion of the ground contacting surface 8, and configured to receive echoes from that surface portion indicative of its topography.

It is contemplated that each of the three phased array ultrasonic sensors 38$x$, 38$y$, and 38$z$ may sweep its respective beam of ultrasonic pulses generally in one of the x, y, and z directions in a three dimensional coordinate system, i.e., generally in three mutually perpendicular directions, so as to cover substantially the entire ground contacting surface S of GET 24. Depending on the specific shape of the ground engaging tool, the directions may vary from general x, y, z coordinate directions. In addition, embodiments wherein two, or more than three, phased array ultrasonic sensors may be employed are contemplated, again depending on the specific shape of the ground engaging tool, for example.

Monitoring component 44 may be configured to receive signals from the phased array ultrasonic sensor 38 and monitor the topography of the surface of GET 24. Monitoring component 44 may include a controller 52. Controller 52 may include a single microprocessor or multiple microprocessors configured to control operation of topographic wear monitoring system 36. Conventional and commercially available microprocessors can be configured to serve as controller 52, perform calculations and comparisons, and perform the control operations required. It should he appreciated that controller 52 could readily be embodied in a general machine microprocessor capable of controlling any number of other machine functions. Controller 52 may include a memory, a secondary storage device, a processor, and any other components for running an application and/or recording signals from sensor 38. Controller 52. may include on-board memory storage for the collection of data received from sensor 38. Various other circuits may be associated with monitoring component 44 and controller 52 such as power supply circuitry, signal conditioning circuitry, solenoid driver circuitry, and other types of circuitry.

One or more maps relating signals received from sensor 38 with wear values for GET 24 may be stored in the memory of controller 52. Controller 52 may be configured to select specific maps from those available to automatically make determinations and/or generate signals regarding topographic wear. The signals generated by controller 52 may be in the form of images on a display 54 located within on-board operator station 18. The signals may be one of audible and visual signals proximate on-board operator station 18 relating to a current topography of the surface S or a portion of the surface of GET 24, a remaining useful life of GET 24, a need to replace GET 24 or its wear tip 28, and/or other parameters and characteristics of GET 24. In this manner, the operator may be able to schedule maintenance of machine 10, or maintenance may be scheduled automatically, in advance of when GET 24 is completely worn out or has otherwise exhibited substantial failure. The signals generated by controller 52 also may function to control one or more of stoppage of machine operation, shut-down of the machine, and shut-down of an associated crusher into which machine 10 may be dumping material.

The signals also may be relayed to an off-board facility 56 via a communication unit 58 associated with controller 52. Communication unit 58 may be configured to communicate messages wirelessly between controller 52 and off-board facility 56. The wireless communications may include satellite, cellular, infrared, and any other type of wireless communication. Off-board facility 56 may include, for example, service personnel, and the communications may include messages regarding wear values, identification of worn components (e.g., particular ones of several GETs 24), and/or instructions for the service personnel. The instructions may be associated with directing the service personnel to provide quotes for replacement components and/or to schedule service of machine 10.

Figure 4:
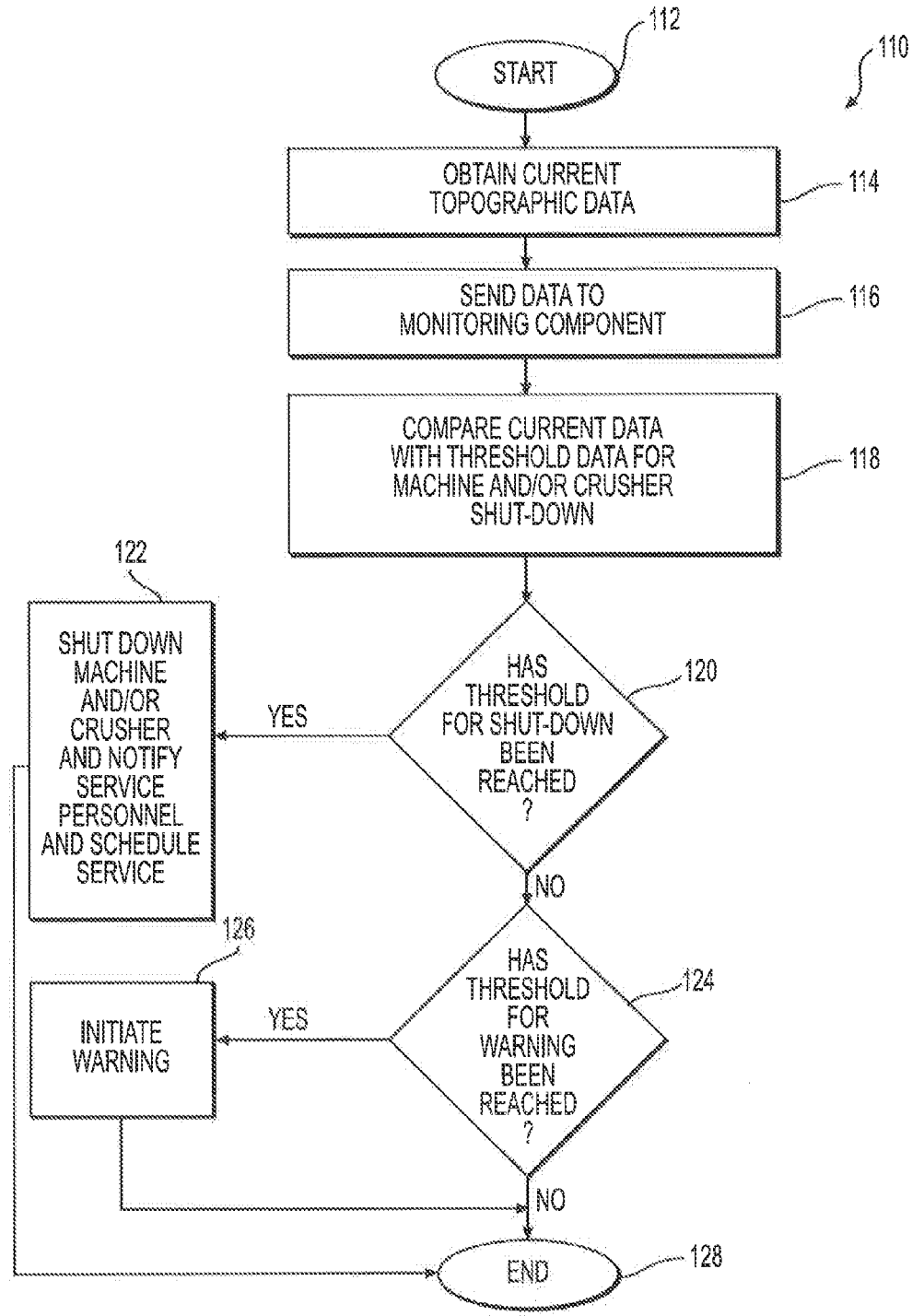
FIG. 4 is an exemplary flow chart in accordance with a disclosed embodiment.

FIG. 4 is a simplified flow chart 110 illustrating one example of implementation of the topographic wear monitoring system 36 according to the disclosure. Referring to FIG. 4, system operation may start at step 112. Current topographic data representing the surface of GET 24 may be obtained at step 114. In accordance with embodiments under the disclosure, this current topographic data may be obtained by one or more phased array ultrasonic sensors 38. For each phased array employed, a beam of pulses may be swept through a volume of GET 24 generally toward a surface portion, the topography of which is to be determined. The time period for echoes to be received back from the surface portion by a sensor 38 will enable calculation of the distance to points on the surface portion. This calculation may be made by the sensor, or the calculation can be made at the monitoring component 44.

Data from sensor 38 may be sent via communication device 40 to monitoring component 44 at 116. Monitoring component 44, for example via controller 52, may compare the current topographic data received with various threshold topographic data representing an unworn GET 24 and/or various degrees of wear of the surface of GET 24. For example, at step 118, monitoring component 44 may compare current data with threshold data for machine and/or crusher shut-down. Monitoring component 44 may store maps representing GET 24 in an unworn condition and/or at various stages of topographic wear and representing various thresholds requiring, for example, a warning or machine shut-down. At step 120, monitoring component 44 makes a determination whether current topographic data exceeds a predetermined threshold that may require shut-down of machine 10 and/or a crusher associated with machine 10 into which machine 10 dumps material. Stated differently, at step 120, monitoring component 44 determines if the difference between current data and an unworn GET exceeds the threshold for shut-down.

Monitoring system 36 is configured to shut down the machine and/or an associated crusher when the comparison indicates a change from a threshold topography that is consistent with a predetermined change that is indicative of substantial failure of the ground engaging tool 24. If, upon executing the comparison at step 118 and the determination at step 120, it is determined that the predetermined threshold for machine and/or crusher shut-down has been reached (step 120: Yes), then one of or both of the machine and crusher may be shut down, at step 122, in order to remove the possibility that work may continue with a defective or failed GET 24 with the concomitant possibility of damage to the crusher. Also at step 122, service personnel may be notified and service may be scheduled. Monitoring system 36 includes controller 52 configured to make decisions, based on received signals, whether to give a warning based on the comparison, shut down the machine based on the comparison, and/or shut down a crusher associated with the machine. If it is determined at step 120 that the predetermined threshold for machine and/or crusher shut-down has not been reached (step 120; No), then a substantially simultaneous determination may be made whether the current threshold exceeds a predetermined threshold that may require that a warning be initiated, at step 124. In other words, at step 124, monitoring component 44 determines if the difference between current data and an unworn GET exceeds the threshold for issuing a warning.

If it is determined at step 124 that the predetermined threshold for a warning has been reached (step 124: Yes), then monitoring component 44 may initiate a warning signal, at step 126. The warning may be a visual indication, e.g., a flashing light; an audible indication, e.g., a buzzer or computer simulated voice warning; an image on display 54, for example a topographic three-dimensional map image; a relayed warning to off-board facility 56 to notify service personnel, for example; or any other type of warning. The warning signal may be one or both of an audible and a visual signal proximate the on-board operator station and generated when the comparison indicates a change in topography consistent with a predetermined difference from an original topography of the ground engaging tool. Along with the warning at step 126, monitoring component 44, for example via controller 52 and communication unit 58, may schedule maintenance and/or inspection by service personnel. For example, the warning may be coupled with a signal indicating a time period within which the machine should be inspected for servicing. If the determination at step 124 is that the predetermined threshold for a warning has not been reached (step 124: No), the sequence of operations ends at 128.

It should be understood that the operations and the sequence thereof as illustrated diagrammatically in FIG. 4 and described above are merely exemplary. Other operations may occur, and in a different sequence. For example, it is contemplated that monitoring component 44 may initiate a display, e.g. on display 54, of an image of GET 24 periodically to give the machine operator regular notice of change in GET 24 topography. This information also may be communicated to off-board facility 56 to notify supervisory or design personnel on an on-going basis. In addition, threshold determinations are not limited to those requiring a warning or machine/crusher shut-down. Maps consistent with thresholds for amount of useful life left in a GET 24 may be included at monitoring component 44 and notifications may be relayed to appropriate design and engineering personnel as determinations are made that these thresholds have been reached. In addition, an electronic record may be generated by monitoring component 44 enabling later analysis of GET topographic wear characteristics.

INDUSTRIAL APPLICABILITY

The disclosed topographic wear monitoring system may be used with any machine having a ground engaging tool that may experience topographic wear of its surface. The disclosed topographic wear monitoring system may be capable of determining a current topography of a GET, an amount of useful life remaining in the GET, a wear rate of the GET, failure or imminent failure of the GET, etc. The disclosed topographic wear monitoring system also may be capable of generating signals indicating or representing these parameters and/or communicating signals to an off-board facility. The signals may be generated continuously, or they may be generated only after a comparison with one or more threshold values indicating the need to generate the signals (e.g., only when the remaining useful life is less than a predetermined threshold, or current topography of the GET indicates wear greater than a predetermined threshold topography).

Topographic wear sensor 38 may be assembled into a cavity in GET 24 that is an extension of an existing recess of the disclosed ground engaging tools. Accordingly, the process used to fabricate the ground engaging tools may require only nominal modification (i.e., to extend the recess far enough to provide the cavity). Where a separate cavity is formed in a wear tip, adapter, or in a single-piece GET, such a separate cavity can be formed during the forming process of the tool, or by a separate milling or boring process, for example. Inasmuch as sensor 38 may remain usable even after GET 24 has reached the end of its useful life, it is possible to reuse the sensor, if desired. Sensor 38 may generate pulses and sweep a beam at a frequency consistent with normally expected wear of the surface of GET 24. Where a GET is on a machine operating under conditions that tend to generate a relatively low wear rate, sensor 38 may be configured to generate pulses and sweep a beam through a volume of the GET spaced apart in time consistent with that rate of wear. On the other hand, where a GET is on a large machine operating continuously in a highly abrasive material environment, sensor 38 may be configured to generate pulses and sweep a beam through a volume of the GET continuously or with very little time between pulses.

The disclosed topographic wear monitoring system may enable development of more efficient and effective ground engaging tools tailored to better fit particular conditions of operation. By sensing and mapping GET wear topography and otherwise generating data representative of topographic wear, tool designers may be able to develop accurate three-dimensional models and digital models representing a GET, to better analyze tool wear, and to better determine appropriate alloys and hard facing materials to employ on a GET in order to extend tool life. Understanding the topographic wear and thus tool performance in field conditions may help answer such questions as whether a GET is staying sharp, losing thickness, changing topography and eroding at a particular surface portion, etc. Topographic wear data may help with strategic planning for supply of replacement tools and for scheduling down-time for machines.

It will be apparent to those skilled in the art that various modifications and variations can be made to the topographic wear monitoring system of the present disclosure without departing from the scope of the disclosure. Other embodiments will be apparent to those skilled in the art from consideration of the specification and practice employing the topographic wear monitoring system disclosed herein. It is intended that the specification and examples be considered as exemplary only, with a true scope of the disclosure being indicated by the following claims and their equivalent.

What is claimed is:

1. A system for measuring topography of the surface of a ground engaging tool, comprising:
    a machine including an on-board station and the ground engaging tool;
    a phased array ultrasonic sensor mounted within the ground engaging tool of the machine and configured to create ultrasonic pulses within the ground engaging tool;
    a communication device associated with the phased array ultrasonic sensor; and
    a monitoring component associated with the on-board station and communicating with the phased array ultrasonic sensor via the communication device, and configured to receive signals from the phased array ultrasonic sensor and monitor the topography of the surface of the ground engaging tool.

2. The system of claim 1, wherein the phased array ultrasonic sensor is attached within a cavity in the ground engaging tool.

3. The system of claim 1, wherein the ground engaging tool is a multi-piece tooth assembly including an adapter and a wear tip, and wherein the phased array ultrasonic sensor is mounted within a cavity in the wear tip.

4. The system of claim 1, wherein the phased array ultrasonic sensor is mounted interiorly of the ground engaging tool and is configured to direct ultrasonic pulses in at least one general direction within the ground engaging tool.

5. The system of claim 4, further including multiple phased array ultrasonic sensors mounted interiorly of the ground engaging tool, and wherein each of the multiple phased array ultrasonic sensors is configured to direct ultrasonic pulses in different general directions within the ground engaging tool.

6. The system of claim 5, wherein the multiple phased array ultrasonic sensors include at least three sensors, and wherein each of the three sensors is configured to direct ultrasonic pulses generally in one of three mutually perpendicular directions.

7. The system of claim 1, wherein the phased array ultrasonic sensor is configured to create ultrasonic pulses within the ground engaging tool at a timing consistent with an expected rate of wear of the tool.

8. The system of claim 1, wherein the communication device is a wireless communication device, and a battery is associated with the phased array ultrasonic sensor and the wireless communication device, and wherein the battery, the phased array ultrasonic sensor, and the wireless communication device are mounted together within a cavity formed interiorly of the ground engaging tool.

9. The system of claim 1, wherein the monitoring component is configured to:
    determine the topography of the surface of the ground engaging tool; make a comparison of the determined topography with a threshold topography; and generate a signal based on the result of the comparison.

10. The system of claim 9, wherein the signal is one of an audible and a visual signal proximate the on-board station and is generated when the comparison indicates a change in topography consistent with a predetermine difference from an original topography of the ground engaging tool.

11. The system of claim 9, wherein the monitoring component is configured to communicate the results of the comparison and the signal to an off-board facility.

12. The system of claim 9, wherein the monitoring component is configured to shut down the machine when the comparison indicates a change in topography that is consistent with a predetermined change that is indicative of substantial failure of the ground engaging tool.

13. The system of claim 9, wherein the monitoring component includes a controller configured to make decisions, based on the received signals, whether to give a warning based on the comparison, shut down the machine based on the comparison, and/or shut down a crusher associated with the machine.

14. The system of claim 13, wherein the warning is coupled with a signal indicating a time period within which the machine should be inspected for servicing.

15. A ground engaging tool for a machine, comprising:
a ground contacting surface surrounding a volume;
a cavity within the ground engaging tool; and
at least one phased array ultrasonic sensor located within the cavity and configured to sweep a beam of ultrasonic pulses through at least a portion of the volume of the ground engaging tool in at least one general direction to at least a portion of the ground contacting surface, and configured to receive echoes from the surface portion indicative of the topography of the surface portion.

16. The ground engaging tool of claim 15, further including a second phased array ultrasonic sensor located within the cavity and configured to sweep a beam of ultrasonic pulses through a second portion of the volume of the ground engaging tool in a second general direction different from the first general direction to a second portion of the ground contacting surface, and configured to receive echoes from the second surface portion indicative of the topography of the second surface portion.

17. The ground engaging tool of claim 16, further including a third phased array ultrasonic sensor located within the cavity and configured to sweep a beam of ultrasonic pulses through a third portion of the volume of the ground engaging tool in a third general direction different from the first and second general directions to a third portion of the ground contacting surface, and configured to receive echoes from the third surface portion indicative of the topography of the third surface portion.

18. The ground engaging tool of claim 17, wherein, the first, second, and third general directions are mutually perpendicular, and the echoes from the first, second, and third surface portions are indicative of the topography of substantially the entire ground engaging surface.

19. A machine, comprising:
an implement operatively associated with the machine;
a ground engaging tool on the implement and including a ground engaging surface;
a cavity within the ground engaging tool;
at least three phased array ultrasonic sensors located within the cavity and configured to sweep beams of ultrasonic pulses through the ground engaging tool, with each of the three phased array ultrasonic sensors located and arranged to sweep beams in three generally, mutually perpendicular directions toward surface portions of the ground engaging tool located in the three directions, and configured to receive echoes from the surface portions giving an indication of the topography of the ground engaging surface;
a wireless communication device located in the cavity, and at least one battery configured to power the wireless communication device and the three phased array ultrasonic sensors; and
a monitoring system configured to determine the topography of the surface of the ground engaging tool, make a comparison of the determined topography with a threshold topography, and generate a signal based on the result of the comparison.

20. The machine of claim 19, wherein the generated signal produces at least one of a visual indication, an audible indication, an electronic record, and a topographic three-dimensional map image on a display, and the monitoring system is configured to shut down the machine when the comparison indicates a change in topography from the threshold topography that is consistent with substantial failure of the ground engaging tool.

* * * * *